United States Patent [19]

Jackson

[11] 4,421,858
[45] Dec. 20, 1983

[54] METHOD FOR DETERMINING THE CONCENTRATION OF SELECTED INGREDIENTS IN ANIMAL FEEDS

[75] Inventor: Dennis E. Jackson, Springfield, Mo.

[73] Assignee: Cambridge Products, Ltd., Springfield, Mo.

[21] Appl. No.: 281,979

[22] Filed: Jul. 10, 1981

[51] Int. Cl.³ .................. G01N 33/02; G01N 31/02
[52] U.S. Cl. .................. 436/20; 426/231; 426/807; 436/56; 436/112; 436/164; 436/177
[58] Field of Search .......... 23/230 R, 230 M, 230 B; 422/56, 68; 426/231, 232, 250, 807; 436/56, 112, 164, 177

[56] References Cited

U.S. PATENT DOCUMENTS 2,157,755  5/1939  Harrel et al. .................. 426/73
2,712,997  7/1955  Cooley .......................... 426/231
3,915,637  10/1975  Taylor .......................... 23/230 B
3,971,855  7/1976  Jackson ......................... 426/807

Primary Examiner—Michael S. Marcus
Attorney, Agent, or Firm—Birch, Stewart, Kolasch & Birch

[57] ABSTRACT

The present invention describes a method where, by using gentian violet as a tracer substance, the concentration of one or more selected components or factors of a complete animal feedstuff may be monitored throughout the life of the feed whether at the mill, in transit or at the place of its end use. In one embodiment, the method may be used to determine quickly whether any separation of components has occurred thereby destroying the homogeneity of the feedstuff and potentially endangering the animals to which the feedstuff is provided.

14 Claims, 1 Drawing Figure

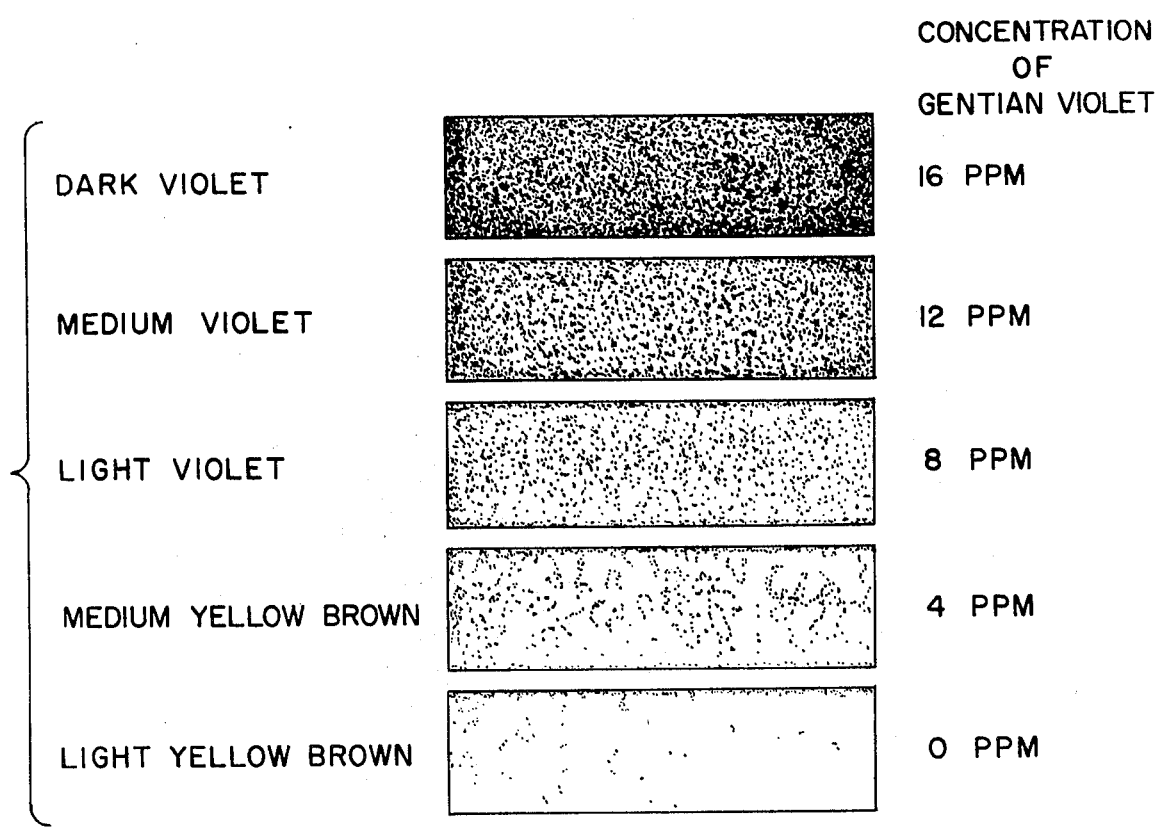

METHOD FOR DETERMINING THE CONCENTRATION OF SELECTED INGREDIENTS IN ANIMAL FEEDS

BACKGROUND OF THE INVENTION

1. Field of the Invention

The present invention is directed generally to a method for determining the concentration of a selected ingredient in complete animal feeds and is more particularly concerned with a novel method for performing such analyses utilizing gentian violet as a tracer substance.

2. Prior Art

The animals, cattle, swine and poultry, that are used most commonly today for production of meat and dairy products are specially bred and raised descendants from animals that once lived naturally in the environment. In recent years, the methods by which such livestock are raised particularly for meat production, have advanced very rapidly. The methods and the associated equipment utilized today have achieved a considerable level of sophistication and have, concomitantly, caused the removal of the animals from their natural environment. In particular, the animals are confined generally to very small areas throughout their growth periods. This forced confinement has both benefits and drawbacks. The benefits are that the animals are prevented from using their muscles in such a way to cause the meat produced to be stringy and tough. On the other side, the animals, by being out of their natural environments, must be fed a fortified diet to compensate for the absence of many feed elements formerly provided within their natural environments.

The general intent of the animal production methods now used is to cause the animals to grow to a marketable size as rapidly as possible. Or, the case of those producing dairy products, to mature rapidly and provide a maximum yield for as long a period as possible. As a result, the industries that raise the livestock and those that provide support to them have become highly specialized. Within the livestock industry, this is achieved through careful breeding and adjustment of the artifical environment. The breeding process has tended to create specialized strains of animals that develop rapidly and put on weight appropriate to quality meats. In the support area, careful balancing of the nutrients furnished to the grower for the animal, particularly those nutrients that do not occur in sufficient supply in naturally grown feeds. As a result, the growth periods for the animals to be ready for market, have been reduced significantly.

The diet fortification materials are added to the diet by mixing them with the more conventional feed provided to the animals which provides conventional protein and energy sources. Modern feed formulations require careful and precise fortification formulation to realize fully the increased growth and production capabilities of today's higher producing animal and poultry strains. In the artificial environments being used, failure to achieve minimum standards of feed fortifications can be both wasteful and costly. The diet fortification materials, which are commonly denominated "microingredients", include vitamins, minerals, antibiotics, preventative and/or therapeutic drugs, antioxidants, supplemental amino acids, enzymes, preservatives, flavors, ingredients that are commonly called "unidentified growth factor sources" and other elements that are found to be necessary in particular applications. Poor uniformity, particularly of the diet fortification materials, within the feedstuff can result in inadequate nutritional intake by the animals or possibly even marginally toxic levels of certain microingredients being located in parts of the feed. Such nonuniformities are generally not fatal; however, regardless of whether they represent deficiencies or excesses, they can be economically harmful to the producer.

The microingredients that are added to the animal feed materials are generally prepared as a "premix" for later addition to the feed. The premix is of a particle size that is much smaller than the grain, soybean and other conventional nutrient materials. In order that the animals receive proper mixtures of the ingredients, considerable care must be employed to insure that adequate mixing is accomplished and that nothing occurs thereafter to cause separation of the various ingredients. If a sufficient separation occurs such that the microingredients' concentration in the feedstuff varies significantly from the intended levels, the growth rates for the animals will almost certainly decline.

Problems in homogeneity of the mixed fortified feed can occur from a wide variety of causes. For example, if equipment being utilized for mixing and blending the various feed materials becomes worn, a distinct lack in homogeneity may and probably will gradually develop. For example, the most commonly used type of feed blending equipment is the horizontal ribbon blender. In these blenders, wear can and usually does occur on the mixing blade which can result in spaces of as much as an inch. In such spaces, the feed tends to be static and to avoid mixing.

Moreover, and perhaps more importantly, the automated equipment that is utilized conventionally for mixing the ingredients may, and occasionally does, malfunction for short periods of time. This is a particular problem in measuring the microingredients into the feed. One standard measure of the premix of fortification ingredients that is utilized is about five pounds per ton of feed. Clearly, minor variances in the rate at which the microingredients are dispensed into the feed can cause wide variations in the resultant concentration of those ingredients. For example, if the valve through which the premix is added to the feed is opened for five seconds to allow five pounds of premix to pass into the feed, a variation of half a second resulting from an error in timing or a sticking during the closing or opening of the valve can cause a ten percent variation in the concentration of premix in the ultimate feed.

Even if the original mixing of ingredients occurs properly, it is far from a certainty that the microingredients will remain uniformly mixed until the feed is dispensed to the animals. The particle size of the microingredients is considerably smaller than that of the more conventional nutrients; therefore, during handling of bulk feeds, the ingredients often tend to separate, allowing the larger particles (the nutrients) to sink and the smaller ones (the microingredients) to rise, thereby destroying the homogeneity. This may occur, for example, when the feed is removed by auger from the mixing apparatus to a storage facility.

A more critical problem in the handling occurs when the mixed bulk feed is transported from the storage facility to the farm for feeding to the livestock. The feed is transported in bulk by truck in most instances. Such trips often require travel of forty miles or more, often over less-than-ideal road conditions. The vibration that is caused within the truck in turn will on occasion be sufficient to again cause the particles to separate according to size.

At present, there are no means available for rapidly and inexpensively checking the concentration and/or homogeneity of microingredients in a sample of the mixed feed without furnishing that sample to a testing laboratory, as the typical farm cannot afford the sophisticated testing equipment nor has the technical know-how to use it. As is apparent, such testing procedures are wholly inadequate to insure proper levels of microingredients in mixed feed, either at the feed market, the storage facility or at the farm. Therefore, wide variations in feed mixtures are often fed to livestock without any knowledge being available to the farmer that the feed is, in fact, incorrect, thereby lowering the efficacy of the feeding process and damaging the farmer economically.

SUMMARY OF THE INVENTION

It is, therefore, an object of the present invention to use an inexpensive substance as a tracer in the premix so that the levels of concentration and homogeneity may readily be determined.

It is a further object of the invention to provide an assay procedure in which gentian violet (methyl rosaniline chloride) is the tracer element and to provide an assay procedure that may be accomplished rapidly and inexpensively at the situs of the feed.

These and other objects and advantages are achieved according to the present invention in its broadest aspect through a method which includes the step of thoroughly mixing an amount of gentian violet with a selected animal feedstuff component the distribution of which is desired to be known. When the component is thus labeled with the gentian violet, it is mixed into the animal feedstuff to form a complete animal feedstuff. The amount of gentian violet that is utilized in the mixing procedure is that which is sufficient to provide upon uniform and complete mixing in the animal feedstuff a known concentration of gentian violet is present within the range of about 3 to about 16 parts per million. A sample is taken of the resulting complete animal feedstuff and is placed in a suitable container. A solvent for the gentian violet is added to the container in an amount sufficient to cover the complete animal feedstuff sample. The solvent and feedstuff are then agitated to cause the gentian violet to be extracted from the feedstuff sample. The liquid is then separated from the feedstuff sample. The separated solution is compared colorimetrically to a suitable standard of known concentrations to ascertain the concentration of the gentian violet and, therefore, the selected component in the sample of the resultant complete animal feedstuff.

These and other objects, features and advantages of the present invention will become readily apparent to one of ordinary skill in the art through the following detailed description of the invention, taken together with the accompanying drawing.

BRIEF DESCRIPTION OF THE DRAWING

In the drawing, the single FIGURE is a typical chart for use in determining the concentration of a selected component in an animal feedstuff sample.

DETAILED DESCRIPTION OF THE PREFERRED EMBODIMENTS OF THE INVENTION

Methylnosaniline chloride is known to be an effective mold and fungi inhibitor when incorporated into animal and poultry feed formulations. E.g., see my prior U.S. Pat. Nos. 3,965,266 and 3,971,655 and Hoffman and Scott, U.S. Pat. Nos. 2,946,722 and 3,231,466. Moreover, methylnosaniline chloride has been discovered previously to be effective in preventing candidas albicans in poultry, see Taylor, U.S. Pat. No. 3,916,027, and reducing the effects of aflatoxins, see Taylor, U.S. Pat. No. 4,126,701.

According to the present invention gentian violet otherwise known as methylnosaniline chloride, or crystal violet, is used as a tracer for selected components of animal feeds so that concentration or the homogeneity of concentration of the selected components may be readily and inexpensively ascertained at the situs of the animal feedstuff. While in its broadest aspects, the invention may be used to monitor concentration levels of any feedstuff components, including the cereal grains and soybean factors, it is more particularly directed to applications where the levels of various microingredients (i.e., the premix) in the feed are to be observed.

In its broadest aspects, the invention contemplates within its purview, the use of suitably-sized gentian violet crystals and the application of liquid solutions of gentian violet directly onto the selected factor to be monitored However, in its solid form, gentian violet cannot be uniformly dispersed. The particles are electrostatic and tend to cling together. Preferably, therefore, the gentian violet is associated with particles whose size approximates that of the factor or factors whose concentration and/or distribution are to be monitored. This simulation of size is necessary to cause those particles having gentian violet associated with them to behave during handling in essentially the same manner as the factor being monitored.

As the invention is most particularly directed to the tracing of various microingredients, in the preferred embodiments, the gentian violet is applied to a finely divided carrier of any of a wide variety of substances that can be incorporated into animal or poultry feedstuffs without an adverse effect on the animals or poultry. A preferred method of preparing the gentian violet is that described in my prior disclosure in U.S. Pat. No. 4,044,152, which disclosure is incorporated fully herein by reference as though it were set forth here in its entirety.

Many suitable carriers for the gentian violet exist, such carriers comprise natural minerals such as clays, diatomaceous earths, calcium or magnesium carbonates, phosphates or silicates and mineral salts of both organic and inorganic nature, such as the salts of trace elements compounds commonly added to feedstuffs, e.g., magnesium, copper, iron, manganese, cobalt and zinc sulfates, citrates or choline citrates and combinations thereof. While any non-toxic, finely-divided solids, preferably of a mineral nature can be used, it is obviously advantageous to use those which, individually or in various combination (as in mineral premixes) can be factored into poultry or animal feeds as desirable or commonly used parts of the primary feed formula. The carrier may be a mineral premix or a component of such a premix. Examples of mineral additives and premix formulations are set forth in the aforementioned U.S. Pat. Nos.

2,946,722 and 3,231,466 and other premix formulations are well known in the art. Advantageously, finely divided limestone, dolomite, deflourinated rock phosphate, tricalcium phosphate, dicalcium phosphate or calcium carbonate may be used. Calcium carbonate or ground limestone are preferred materials because in minimal quantities they are components of substantially all formulated feedstuffs and when used as dispersing agents can be calculated by the nutritionist, the result in effect being that virtually no dilution of the nutrient value of the feedstuff occurs as a result of the addition of the gentian violet.

The acid used for treating the carrier is one which in the amounts used will not be harmful, either as such or in the form of its reaction products, in the feed product. The function of the acid, either as such or in the form of its reaction products, is to provide a material which is in intimate association with the gentian violet on the carrier and which will facilitate release of the gentian violet during testing. Organic acids, such as acetic, citric, propionic, butyric and lactic can be used, as well as mineral acids provided they do not form water-insoluble reaction products with the components of the carrier. Ordinary vinegar may be used to supply the acid.

The more finely-divided the carrier material the more thoroughly it can be incorporated into the feedstuff. This, of course, is an important consideration in view of the fact that quantities of additive as small as one-half pound per ton of feed or less may be incorporated in the feed product. The carrier is preferably sufficiently finely divided as to pass through a 100 mesh standard sieve and conveniently is in the minus 325 mesh size range.

The gentian violet is dissolved in a volatile organic solvent, such as an alcohol or ketone, for dispersion on the carrier. The acid can be included in the same solvent or can be added to the carrier before or after addition of the gentian violet.

In a typical method of manufacture the gentian violet and acid are both dissolved in the volatile solvent and the resulting solution is added to the dry carrier material in a suitable mixer. Alternatively, separate solutions of gentian violet and acid may be added to the dry ingredients in either order. Mixing can be continued until the materials are thoroughly mixed and the volatile solvent is substantially evaporated. Where reaction occurs between the carrier and acid some heat is given off which aids in the evaporation of the solvent. However, even without heating, a solvent which is sufficiently volatile, such as methyl alcohol, will substantially evaporate during mixing.

According to the present invention, an amount of the gentian violet labeled carrier is mixed with the feedstuff factor to be monitored, after which the carrier and factor are mixed with the remaining feedstuff factors to form the final complete feedstuff product. In view of the fact that the factors to be monitored are preferably those of various microingredients in the preferred embodiments of the present invention, the labeled carrier is introduced into and mixed with a premix that includes the various microingredients.

The amount of labeled carrier that is introduced, whether mixed initially with a premix or with a single feed factor, is of an amount sufficient to cause from about three to sixteen parts per million of the gentian violet to be present in the resulting complete animal feedstuff, assuming that the feed factors have been distributed homogeneously. Preferably, a level of about four to ten parts per million of gentian violet is achieved throughout the final complete feedstuff with four parts per million being the most desirable.

EXAMPLE 1

A finely divided carrier is treated as described above such that 1.6 percent by weight of gentian violet is contained in it for use as a labeling material. In a premix formulation that is used at the rate of 25 kg/tonne of complete feed, 10 kilograms of labeled gentian violet carrier is mixed into each tonne of the premix. The resulting complete animal feedstuff contains approximately four parts per million of gentian violet.

EXAMPLE 2

The same labeled carrier as in Example 1 is added to a supplement or concentrate that is utilized at the rate of 200 kh/tonne. Here, 1.25 kg of the gentian violet labeled carrier is added to each tonne of the supplement or concentrate resulting in a concentration of about four parts per million in the complete animal feedstuff.

As thus provided in animal and poultry feedstuffs, I have discovered that the level of concentration of the ingredients may be quickly and accurately determined at the situs of the feed, whether at the mill, in transit or at the ultimate place where the animals or poultry are to be fed. According to the invention, by thoroughly mixing the labeled carrier with a feed factor before addition of that factor to the feed and with the carrier and factor particles being similarly sized, the distribution of the labeled carrier (i.e., the distribution of gentian violet) in the complete feedstuff is highly indicative of the level of the monitored factor in the complete feedstuff.

When it is desired to determine the concentration of the monitored factor in a complete animal or poultry feed, a plurality of separate representative samples are drawn from the feedstuff and are thoroughly blended together. A defined portion of the blended samples is taken and a quantity of a solvent for gentian violet is added thereto. The portion of feedstuff and the solvent are thoroughly agitated to extract the gentian violet. The gentian violet solution is then separated from the solid feedstuff particles. Thereafter, the color of a known, preselected thickness of the gentian violet carrying solvent is compared to a chart to determine directly the concentration of gentian violet in the blended sample, and, more importantly, the concentration of the monitored factor in the samples.

Any liquid in which gentian violet is readily solvent may be used; however, it is preferred that the solvent be an organic solvent such as an alcohol or a ketone. The primary criteria for the solvent is that it be clear so that the color in transmission may be observed and that the gentian violet be readily soluble in it. Methylethyl and butyl alcohols are the presently preferred solvents.

On the other hand, in those instances where the distribution of a factor in a feed is to be monitored, the procedure above is modified to the extent that the representative samples are not blended but rather analyzed separately. After each of the representative samples is analyzed, the results are compared to ascertain whether the monitored factor is uniformly distributed through the feedstuff.

As will be readily apparent to one of ordinary skill in the art, this testing procedure can be carried out quickly by nearly everyone and with a minimum of equipment at any site, regardless of how remote it may be. It is this ease and convenience that provides the primary utility of the invention.

EXAMPLE 3

Three representative samples of approximately 100 grams each are taken from a complete feed in which a gentian violet labeled carrier has been mixed so as to provide theoretically a gentian violet presence of 4 ppm. The three samples are thoroughly blended together. Approximately 10 grams of the blended sample mixture is taken and placed in a 16×125 mm glass test tube. Approximately 8.5 milliliters of methyl alcohol are added to the test tube and shaken vigorously for about 2 minutes to extract the gentian violet from the feed sample. The test tube is then allowed to stand for about 10 minutes to allow the various solid feed factor particles to settle to the bottom of the test tube. The liquid is then decanted into a 12×75 mm glass test tube. The color of the liquid is then compared to a chart such as that shown in the drawing and the concentration of gentian violet (in ppm) determined from the scale. Although the drawing of the present specification is presented in black and white, it will be appreciated that, in use, the chart will comprise a color chart with individual portions varying in shades of violet depending on the concentration of gentian violet. Knowing that a level of 4 ppm was intended, the test permits an immediate determination of the concomitant level of the monitored factor in the feed.

Alternatively, after agitating the solvent and sample, the solvent may be separated from the solid feed particles by filtration. However, filtration is not preferred as it requires additional equipment to be available at the test site, although it does allow for the test to be completed somewhat more quickly.

As can readily be appreciated from the drawing, gentian violet is a particularly effective agent for use in a field testing method because of the distinct color differences that exist at various levels of concentration thereby allowing for easy extrapolation of intermediate values by even an unskilled operator.

EXAMPLE 4

A test was conducted to establish the accuracy of field testing for gentian violet concentration and to determine if the method of the invention was suitable for conduction by the end user of the feedstuff. In the test, visual scoring results using the method of the present invention performed by untrained operators, were compared to spectrophotometric results accomplished conventionally in a laboratory. Results of the two field kit scores were averaged for analysis, and all results were analyzed by standard statistical methods using a TI-59 statistical package. Due to zero values, all data was transformed by the formula $n=(n+1)$ before analysis.

Six samples of approximately 1000 g each were taken from three differing feed types—layer, broiler and swine. The eighteen samples were placed in polyethylene bags. To five of the six samples of each feed type were added either 125 mg, 250 mg, 375 mg, 500 mg or 625 mg of a gentian violet labeled carrier thereby producing samples containing 0, 2, 4, 6, 8 or 10 ppm of gentian violet within each feed type. The samples were mixed by inflating and repeatedly tumbling the bags. After mixing, four 100 g representative samples were withdrawn from each bag and placed in glass, screw-topped jars previously coded with numbers. The key to the code was retained by the person withdrawing the samples to preclude bias in the analysis.

Table I below shows the actual results of the assays performed in the laboratory and by the visual method of the present invention. The visual results show each of the two readings achieved by the operators and the average reading within brackets.

TABLE I

| Theory | FEED TYPE 1 (layer) | | | FEED TYPE II (broiler) | | | FEED TYPE III (swine) | | |
|---|---|---|---|---|---|---|---|---|---|
| | Lab | Visual | | Lab | Visual | | Lab | Visual | |
| 0 | 0 | 2/0 | (1) | 0 | 0/0 | (0) | 0 | 0/0 | (0) |
| | 0 | 0/2 | (1) | 0 | 0/0 | (0) | 0 | 0/0 | (0) |
| | 0 | 0/0 | (0) | 0 | 2/0 | (1) | 0 | 0/0 | (0) |
| | 0 | 0/0 | (0) | 0.02 | 0/2 | (1) | 0 | 0/0 | (0) |
| 2 | 1.85 | 2/2 | (2) | 1.95 | 2/2 | (2) | 2.10 | 2/0 | (1) |
| | 1.80 | 4/4 | (4) | 2.15 | 2/2 | (2) | 2.00 | 2/2 | (2) |
| | 1.95 | 4/2 | (3) | 1.90 | 2/0 | (1) | 2.15 | 2/2 | (2) |
| | 1.90 | 4/4 | (4) | 1.85 | 2/2 | (2) | 2.10 | 2/0 | (1) |
| 4 | 3.95 | 4/4 | (4) | 4.05 | 2/4 | (3) | 2.00 | 4/2 | (3) |
| | 4.10 | 6/4 | (5) | 3.80 | 4/4 | (4) | 3.85 | 4/6 | (5) |
| | 4.20 | 4/6 | (5) | 3.85 | 4/4 | (4) | 3.95 | 4/4 | (4) |
| | 4.05 | 4/4 | (4) | 3.90 | 4/4 | (4) | 4.05 | 4/4 | (4) |
| 6 | 6.10 | 6/6 | (6) | 5.75 | 6/6 | (6) | 6.00 | 6/6 | (6) |
| | 6.00 | 6/6 | (6) | 5.70 | 6/4 | (5) | 6.00 | 4/6 | (5) |
| | 6.05 | 4/6 | (5) | 5.65 | 4/6 | (5) | 6.15 | 6/6 | (6) |
| | 6.15 | 4/6 | (5) | 5.80 | 6/6 | (6) | 6.20 | 6/6 | (6) |
| 8 | 7.90 | 8/8+ | (9) | 8.00 | 8/8 | (8) | 7.75 | 8/8 | (9) |
| | 7.85 | 8/8 | (8) | 8.50 | 8+/8 | (9) | 7.75 | 8/8 | (9) |
| | 7.85 | 8/8 | (8) | 8.10 | 8/8 | (8) | 7.80 | 8+/8 | (9) |
| | 7.75 | 8/8 | (8) | 8.15 | 8/8 | (8) | 7.75 | 8/8 | (8) |
| 10 | 9.55 | 8+/8 | (9) | 10.15 | 8+/8+ | (10) | 9.70 | 8+/8+ | (10) |
| | 9.70 | 8/8+ | (9) | 10.05 | 8+/8 | (9) | 9.80 | 8+/8+ | (10) |
| | 9.75 | 8+/8+ | (10) | 10.00 | 8+/8 | (9) | 10.10 | 8+/8+ | (10) |
| | 9.45 | 8/8+ | (9) | 10.15 | 8+/8+ | (10) | 9.95 | 8+/8+ | (10) |

Table II summarizes the results of the field test method of the present invention and provides the statistical parameters attendant to those results.

TABLE II

| Theory (ppm) | FEED TYPE 1 field kit (ppm) | FEED TYPE II field kit (ppm) | FEED TYPE III field kit (ppm) |
|---|---|---|---|
| 0 | 0.5 ± 0.926 | 0.5 ± 0.926 | 0 ± 0.0 |

TABLE II-continued

| Theory (ppm) | FEED TYPE 1 field kit (ppm) | FEED TYPE II field kit (ppm) | FEED TYPE III field kit (ppm) |
|---|---|---|---|
| 2 | 3.25 ± 1.035 | 2.75 ± 0.707 | 1.50 ± 0.926 |
| 4 | 4.50 ± 0.926 | 3.75 ± 0.707 | 4.00 ± 1.069 |
| 6 | 5.50 ± 0.926 | 5.5 ± 0.926 | 5.75 ± 0.707 |
| 8 | 8.125 ± 0.354 | 8.25 ± 0.707 | 8.25 ± 0.707 |
| 10 | 9.25 ± 1.035 | 9.75 ± 0.707 | 10.00 ± 0.00 |

Table III illustrates the accuracy of the two operators using the present invention. The raw score is reached by scoring a "1" whenever the operator reached a correct reading versus the "theory" level, thereby having a maximum possible score of 24. An incorrect reading resulted "0" score. The correlation coefficient (r) relates the laboratory results to the average of the field test scores.

TABLE III

| | FEED TYPE 1 | | FEED TYPE II | | FEED TYPE III | |
|---|---|---|---|---|---|---|
| | OP 1 | OP 2 | OP 1 | OP 2 | OP 1 | OP 2 |
| Raw Score | 15 | 17 | 20 | 19 | 22 | 20 |
| Correlation Coefficient (r) | 0.973 | | 0.987 | | 0.985 | |

Finally, Table IV shows the correlation coefficients between the laboratory spectrophotometric assays and the operator field test results for each level of gentian violet concentration and across all three of the feed types. This data is considered to be a reliable measure of the accuracy obtained by the operators using the present invention.

TABLE IV

| Theory (ppm) | (r) |
|---|---|
| 0 | 0.426 |
| 2 | −0.501 |
| 4 | 0.140 |
| 6 | 0.244 |
| 8 | 0.678 |
| 10 | 0.544 |

Regression analysis of the laboratory results versus the field test average scores provided an overall correlation of 0.982, a totally acceptable result.

The poorest results from the visual test occurred with Feed Type I, a layer type. This feed contained some dehydrated alfalfa meal, a highly pigmented ingredient which increased background color. Other pigmented feeds (containing, e.g., grass meal or corn gluten meal) may also cause some interference with the field assay of the present invention.

As is readily apparent from the foregoing tables, the accuracy of the field tests improved as the concentration levels reached the range of 4 to 10 ppm. Levels below about 3 ppm have too little color for effective analysis. Conversely, above 16 ppm, the depth of color prohibits accurate readings to be taken. Therefore, this range is believed to be preferable for the practicing of the present invention.

While there have been described what are presently considered to be preferred embodiments of the present invention it will be obvious to those of ordinary skill in the art that various changes and modifications may be made therein without departing from the invention as defined in the appended claims.

I claim:

1. A method for measuring the concentration of a selected finely-divided, dry component of an animal feedstuff comprising the steps performed in the following order;
   (a) dispersing gentian violet on a finely-divided carrier, the carrier particles being of approximately the same size as those of the selected components;
   (b) admixing thoroughly an amount of gentian violet bearing carrier to the selected animal feedstuff component to label the component;
   (c) admixing the labeled component into the animal feedstuff to form a complete animal feedstuff, the quanitity of gentian violet being sufficient to provide, upon complete mixture, a known concentration in the resultant animal feedstuff in the range from about 3 to about 16 parts per million;
   (d) selecting a sample of the resultant animal feedstuff and placing it in a container;
   (e) adding a sufficient amount of a solvent for gentian violet to cover the sample;
   (f) agitating the immersed sample sufficiently to extract the gentian violet from the sample;
   (g) separating the gentian violet and solvent from the solid portion of the sample; and
   (h) comparing visually the color of the gentian violet solution of step (g) to a suitagle standard for the known concentration to ascertain the concentration of gentian violet in the sample whereby the concentration of the selected component in the resultant feedstuff may be measured concomitantly at the situs of the resultant animal feedstuff.

2. A method according to claim 1, wherein the selected component is a premix of supplemental nutritional and medicinal values.

3. A method according to claim 2, wherein the solvent is an organic solvent.

4. A method according to claim 3, wherein the concentration of gentian violet in the complete animal feedstuff is in the range from about 4 to 10 parts per million.

5. A method according to claim 4, wherein the concentration of gentian violet in the complete animal feedstuff is approximately 4 parts per million and the organic solvent is selected from the group consisting of alcohols and ketones.

6. A method according to claim 4, wherein the separation of the gentian violet solution is accomplished by allowing the sample to stand for a period sufficient to permit solids to settle out and decanting the gentian violet solution from the sample.

7. A method according to claim 4, wherein the separation of the gentian violet solution is accomplished by filtration.

8. A method according to claim 2, wherein the method includes the further steps of selecting a plurality of samples from the complete animal feedstuff, ascertaining the concentration of gentian violet in each sample separately, and comparing the concentrations of gentian violet to ascertain the homogeneity of concentration of the selected component in the complete animal feedstuff.

9. A method according to claim 2, wherein the method further comprises the steps of selecting a plurality of separate samples of the complete animal feedstuff and mixing thoroughly the plurality of samples to eliminate any localized variations in concentration of the premix in the animal feedstuff.

10. A method according to claim 9, wherein at least three samples are selected.

11. A method for measuring the concentration of a finely-divided, dry premix in an animal feedstuff comprising the steps performed in the following order;
   (a) dispersing an amount of gentian violet onto a carrier compatible with the animal feedstuff, which carrier is sufficiently finely divided so as to approximate the size of particles in the premix;
   (b) admixing thoroughly an amount of the gentian violet labeled carrier with the premix to label the premix;
   (c) admixing the labeled premix into the animal feedstuff to form a complete animal feedstuff, the amount of gentian violet being sufficient to provide, upon complete mixture, a known concentration in the resultant complete animal feedstuff in the range from about 4 to about 10 parts per million;
   (d) selecting a sample of the resultant complete animal feedstuff and placing it in a container;
   (e) adding a predetermined amount of an organic solvent for gentian violet selected from the group consisting of alcohols and ketones to the sample;
   (f) agitating the immersed sample sufficiently to extract the gentian violet from the sample;
   (g) allowing the sample to stand for a period sufficient to permit solids to settle out;
   (h) decanting the gentian violet and solvent from the sample; and
   (i) comparing visually the color of the gentian violet solution of step to a suitable standard for the known concentrations to ascertain the concentration of gentian violet in the sample whereby the concentration of the premix component in the resultant complete animal feedstuff may be measured concomitantly at the situs of the resultant animal feedstuff.

12. A method according to claim 11, wherein the method is utilized to monitor the homogeneity of concentration of the premix and includes the further steps of selecting a plurality of samples from the complete animal feedstuff, ascertaining the concentration of gentian violet in each sample separately, and comparing the concentrations of gentian violet to ascertain the homogeneity of concentration of the selected component in the complete animal feedstuff.

13. A method according to claim 11, wherein the method further comprises the steps of selecting a plurality of separate samples of the complete animal feedstuff and mixing thoroughly the plurality of samples to eliminate any localized variations in concentration of the premix in the animal feedstuff.

14. A method according to claim 13, wherein at least three samples are selected.

* * * * *